(12) United States Patent
Au

(10) Patent No.: US 10,709,514 B2
(45) Date of Patent: Jul. 14, 2020

(54) FLEXIBLE MEDICAL INSTRUMENT

(71) Applicant: INTUITIVE SURGICAL OPERATIONS, INC., Sunnyvale, CA (US)

(72) Inventor: Samuel Kwok Wai Au, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 232 days.

(21) Appl. No.: 15/509,154

(22) PCT Filed: Sep. 3, 2015

(86) PCT No.: PCT/US2015/048252
§ 371 (c)(1),
(2) Date: Mar. 6, 2017

(87) PCT Pub. No.: WO2016/040079
PCT Pub. Date: Mar. 17, 2016

(65) Prior Publication Data
US 2017/0281288 A1 Oct. 5, 2017

Related U.S. Application Data

(60) Provisional application No. 62/048,194, filed on Sep. 9, 2014.

(51) Int. Cl.
*A61B 1/00* (2006.01)
*A61B 34/35* (2016.01)
(Continued)

(52) U.S. Cl.
CPC ............ *A61B 34/35* (2016.02); *A61B 1/0016* (2013.01); *A61B 1/00078* (2013.01);
(Continued)

(58) Field of Classification Search
CPC . A61B 1/0006; A61B 1/00078; A61B 1/0016; A61B 1/0051; A61B 1/0053;
(Continued)

(56) References Cited

U.S. PATENT DOCUMENTS 6,890,297 B2  5/2005  Belson
2002/0095175 A1  7/2002  Brock et al.
(Continued)

FOREIGN PATENT DOCUMENTS

CN  102449666 A  5/2012
EP  0077526 A2  4/1983
(Continued)

OTHER PUBLICATIONS

Extended European Search Report for Application No. EP15839801. 6, dated May 29, 2018, 13 pages.
(Continued)

*Primary Examiner* — Dale Moyer
(74) *Attorney, Agent, or Firm* — Haynes and Boone, LLP

(57) ABSTRACT

A medical system including a flexible instrument such as a lung catheter or bronchoscope provides a control mode in which direct manual control of insertion can be used with computer-assisted control of instrument characteristics such as the orientation or rigidity of a portion of the instrument. To facilitate manual insertion control, a mechanism can provide low inertia and friction for movement along an insertion axis. One implementation employs a manual grip of the instrument for control of insertion pressure, a joystick or other input device for computer-assisted steering, and a foot pedal for control of stiffness or compliance in the instrument. Another implementation employs a joystick for computer-assisted steering and for control of stiffness or compliance in the instrument.

17 Claims, 3 Drawing Sheets

(51) Int. Cl.
*A61B 34/30* (2016.01)
*A61B 34/00* (2016.01)
*A61M 16/04* (2006.01)
*A61B 1/005* (2006.01)
*A61B 1/267* (2006.01)

(52) U.S. Cl.
CPC .............. *A61B 34/30* (2016.02); *A61B 34/71* (2016.02); *A61B 34/74* (2016.02); *A61B 1/00006* (2013.01); *A61B 1/0053* (2013.01); *A61B 1/0057* (2013.01); *A61B 1/2676* (2013.01); *A61B 34/76* (2016.02); *A61B 2034/301* (2016.02); *A61B 2034/742* (2016.02); *A61M 16/04* (2013.01)

(58) Field of Classification Search
CPC ..... A61B 1/0057; A61B 1/2676; A61B 34/30; A61B 2034/301; A61B 34/35; A61B 34/71; A61B 34/74; A61B 2034/742; A61B 34/76
See application file for complete search history.

(56) References Cited

U.S. PATENT DOCUMENTS

| | | |
|---|---|---|
| 2003/0195389 A1 | 10/2003 | Motoki et al. |
| 2006/0058647 A1 | 3/2006 | Strommer et al. |
| 2006/0178563 A1 | 8/2006 | Hirata et al. |
| 2010/0249506 A1* | 9/2010 | Prisco .............. A61B 1/00009 600/117 |
| 2010/0280449 A1 | 11/2010 | Alvarez et al. |
| 2010/0331820 A1 | 12/2010 | Prisco et al. |
| 2011/0071347 A1 | 3/2011 | Rogers et al. |
| 2011/0196199 A1 | 8/2011 | Donhowe et al. |
| 2011/0282491 A1 | 11/2011 | Prisco et al. |
| 2012/0065628 A1* | 3/2012 | Naito .............. A61B 1/00078 606/1 |
| 2012/0123441 A1 | 5/2012 | Au et al. |
| 2012/0184955 A1 | 7/2012 | Pivotto et al. |
| 2012/0283747 A1* | 11/2012 | Popovic .............. A61B 34/30 606/130 |
| 2013/0096497 A1 | 4/2013 | Duindam et al. |
| 2013/0096572 A1* | 4/2013 | Donhowe .............. A61B 34/10 606/130 |
| 2015/0011830 A1* | 1/2015 | Hunter .............. A61B 1/0052 600/118 |
| 2015/0366445 A1* | 12/2015 | Rutgers .............. A61B 1/267 600/120 |
| 2016/0058268 A1* | 3/2016 | Salman .............. A61B 1/0055 600/149 |

FOREIGN PATENT DOCUMENTS

| | | |
|---|---|---|
| EP | 1582139 A2 | 10/2005 |
| JP | 2001286437 A | 10/2001 |
| JP | 2007083038 A | 4/2007 |
| JP | 2011072384 A | 4/2011 |
| WO | WO-2010111090 A1 | 9/2010 |
| WO | WO-2011100110 A1 | 8/2011 |
| WO | WO-2012027581 A2 | 3/2012 |
| WO | WO-2013026012 A1 | 2/2013 |
| WO | WO-2013056006 A2 | 4/2013 |

OTHER PUBLICATIONS

Partial Supplementary European Search Report for Application No. EP15839801.6, dated Mar. 8, 2018, 12 pages.
International Preliminary Report on Patentability for Application No. PCT/US2015/048252, dated Mar. 23, 2017, 8 pages.
International Search Report and Written Opinion for Application No. PCT/US15/048252, dated Dec. 9, 2015, 17 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Office Action dated Mar. 14, 2019 for Chinese Application No. 2015800482596 filed Sep. 3, 2015, 13 pages.

* cited by examiner

FLEXIBLE MEDICAL INSTRUMENT

RELATED APPLICATIONS

This application is the U.S. national phase of International Application No. PCT/US2015/048252, filed Sep. 3, 2015, which designated the U.S. and claims priority to U.S. Provisional Patent Application 62/048,194, filed Sep. 9, 2014, the contents of each of which are incorporated herein by reference.

BACKGROUND

Robotic medical devices have many advantages during medical procedures. (As used herein, the terms "robotic" or "robotically" and the like include teleoperation or telerobotic aspects.) In particular, computer control in a robotic medical device may be able to provide steadier and more precise movement of a tool such as a biopsy needle, scalpel, or clamp. For minimally invasive medical procedures, computer control may also facilitate miniaturization of a tool because the mechanical systems in the tool do not need to be easily hand operable or need to operate intuitively because computerized control systems can adapt to complex or obtuse mechanical systems or interfaces and still provide a human operator with a user interface that is easy to use.

One difficulty for robotic medical devices and their user interfaces is providing human personnel with haptic or tactile feedback. In particular, providing an input device of a computerized system with haptic feedback that is similar or equivalent to the haptic feedback of a manually manipulated medical instrument can be difficult. One example of a situation in which haptic feedback is important is during navigation of an instrument such as a lung catheter, a bronchoscope, a biopsy instrument, or other similar medical device through airways or other branching or convoluted natural lumens. In particular, insertion of an instrument through an airway may experience a challenge that increases resistance to further advancement of the instrument. The tip of the instrument may, for example, need to be reoriented where an airway bends or forks. The haptic or tactile feel that a doctor or other medical practitioner may receive from manually applying insertion pressure gives the practitioner guidance and insight regarding the interaction of the instrument with the airway. The practitioner may then be able to better judge whether or how to further advance the instrument, for example, by applying more insertion force, applying a torque or twist to reorient the instrument and reduce the friction in the airway, or partially or fully retracting the instrument. Haptic feel can be an important or critical factor that the practitioner uses during such decisions. However, standard robotically controlled instrument insertion techniques may provide the practitioner with no, little, or inaccurate tactile or haptic feedback.

SUMMARY

In accordance with an aspect of the invention, a robotically controlled instrument may provide a very low inertia and low friction drive for the insertion of the instrument. During insertion of the instrument and particularly during airway navigation, an insertion drive motor of the instrument may be off, inactive, or operated in a manner that effectively minimizes inertia, and a practitioner may have direct manual, e.g., hands on, control of insertion of the instrument. At the same time, the practitioner may employ robotic pitch-yaw drive systems of the instrument to control the orientation of the distal tip of the instrument. For example, the practitioner may apply insertion pressure through manual manipulation of a distal portion of the instrument and control the tip orientation though a computer interface that receives practitioner input through a joystick or other input device. The active computer controlled system may further provide the practitioner with additional control capabilities such as control of the stiffness of the instrument. In particular, the practitioner may control the rigidity of the inserted length of an instrument, the tip of the instrument, or any portion of the instrument and may reduce rigidity to allow the instrument to conform to a current path of the instrument or increase rigidity of the instrument to better apply insertion pressure.

Instrument stiffness may be adjustable in a manner or through a process that a control instrument employs to control tension in actuating tendons or other structures in the instrument. In one implementation, a foot pedal or other dedicated input device can provide a user control of stiffness of a flexible instrument. In another implementation, a joystick or other input device that a user may manipulate in order to steer the instrument may also provide stiffness control. For example, an input device may have a central or neutral position, e.g., a position that the input device assumes when a user releases the input device, and when the input device is in its neutral position, the control system for the instrument may place the instrument in a low stiffness state. Accordingly, a user that encounters resistance when inserting an instrument in a natural lumen may simply release the input device to allow the flexible instrument to relax and conform to the shape of the natural lumen. After the instrument has relaxed and conformed, resistance to further insertion may be greatly reduced.

Such control systems may provide users with intuitive control of tip stiffness. For example, use of an additional or dedicated input device such as a foot pedal in which the pedal stroke is proportional to the tip stiffness gives the user a simple and natural way to specifically control stiffness. A joystick or other input device can still be used to control orientation of the tip. Alternatively, manipulation of a single input device such as a joystick could control both stiffness and orientation control. For example, one way to implement stiffness control is to map the joystick position, e.g., with respect to the center position with a spring loaded mechanism, to the tip stiffness and relative orientation. A combination of a separate stiffness control and an integrated manipulator and stiffness control could also be employed.

BRIEF DESCRIPTION OF THE DRAWINGS

The drawings illustrate examples for the purpose of explanation and are not of the invention itself. Use of the same reference symbols in different figures indicates similar or identical items.

DETAILED DESCRIPTION

A medical system including a flexible instrument such as a lung catheter or bronchoscope can provide multiple control modes for navigation of natural lumens such as airways. In a computer assisted control mode, a user may manipulate an input device and cause a computer system to control actuators for steering and insertion of the flexible instrument. In a semi-robotic control mode, a user may have direct manual control of insertion pressure and simultaneously manipulate an input device for computer assisted or mechanically actuated control of instrument characteristics such as tip orientation or instrument rigidity or stiffness. To facilitate manual control, a steering drive mechanism of a robotically controlled instrument may be mounted on a low inertia and low friction insertion mechanism, and the insertion drive mechanism may be backdrivable, which allows the instrument to be manually manipulated while preserving the haptic feel from which the practitioner may perceive the interaction between the instrument and the airway. In general, a backdrivable instrument is an instrument having an actuated portion that a user can manually manipulate or operate when the actuator mechanism is off. A user may thus directly manipulate a portion of the instrument with a certain amount of directly applied effort or force. The manual manipulation, e.g., manual insertion, of the instrument generally gives a direct haptic feel for interactions between the instrument and patient tissue. The steering drive mechanism can manipulate pitch and yaw orientation of the distal tip of the instrument and can be controlled precisely by manipulating an input device such as a joystick. The computer assisted control system can also manipulate or control stiffness of all or a portion of the instrument, e.g., a length near the distal tip of the instrument. Stiffness control can be implemented through a separate input device such as a foot pad or pedal that allows a user to vary the stiffness of the controlled portion of the instrument, while independently controlling tip orientation and manually inserting the instrument. For example, a foot pedal may have a released position, e.g., where the pedal is not depressed, in which the backend mechanism provides a tip control mode with high stiffness, while depressing or loading the pedal can reduce stiffness of a distal portion of the instrument up to a lowest stiffness, i.e., highest compliance, state of the distal portion. As an alternative to separate input devices for computer assisted steering and stiffness control, a single input device such as a joystick can control both steering, e.g., stiffness and pitch and yaw orientations of a distal tip of the instrument. For example, a control system may increase the stiffness of the distal tip of the instrument as the input device indicates that the pitch or yaw angles of the distal tip should be increased.

Figure 1:
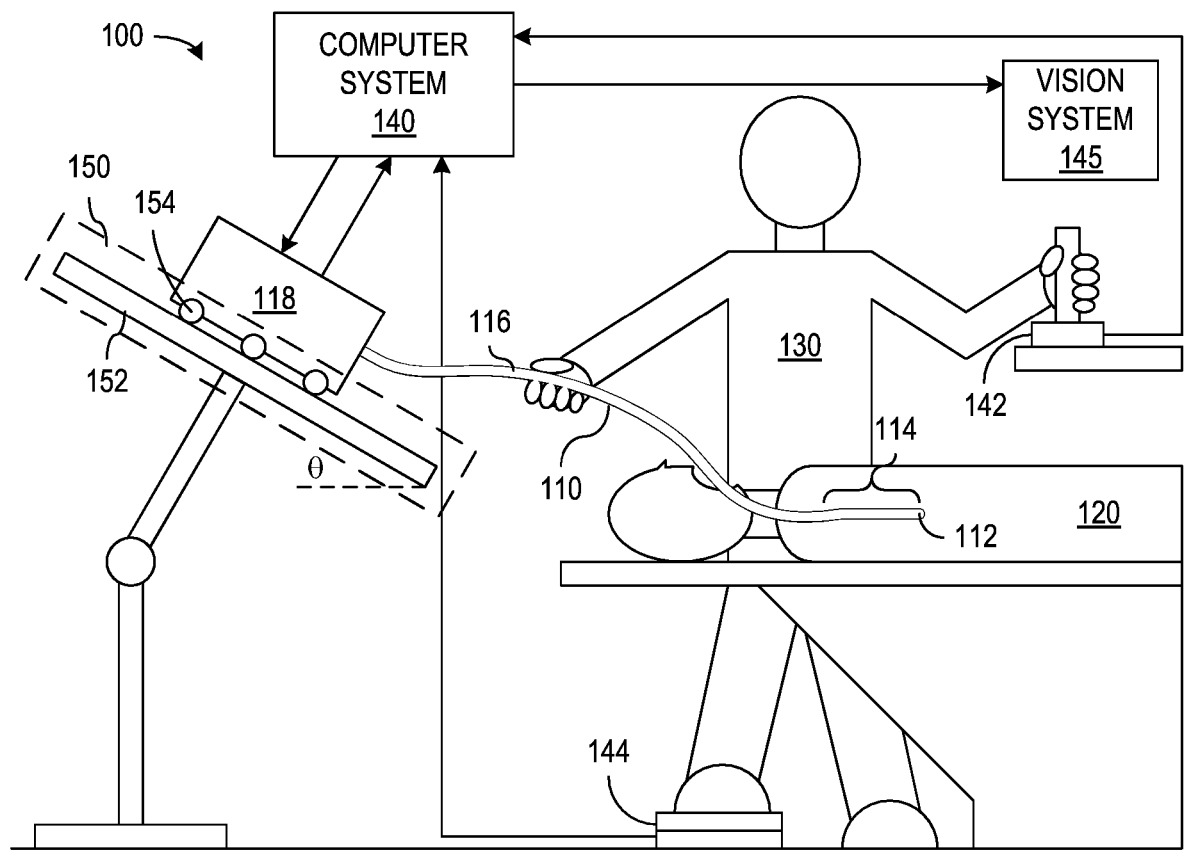
FIG. 1 schematically shows a system in an implementation that permits direct manual control of insertion pressure and computer assisted control of other characteristics of a medical instrument.

FIG. 1 schematically illustrates one implementation of a medical system 100 including a robotically-controlled instrument 110 such as a lung catheter, bronchoscope, or any other flexible instrument having an insertion axis. The insertion axis corresponds to movement of a distal tip 112 of instrument 110 further into a patient 120 or withdrawing distal tip 112 of instrument 110 from patient 120. For example, instrument 110 may be a lung catheter that is used in a procedure such as a biopsy performed on a site in a lung of patient 120, and a user 130 such as a doctor or other medical technician may control instrument 110 with the assistance of a computer system 140 to insert instrument 110 through a mouth of patient 120 and from there to navigate distal tip 112 through airways to the target site that may be in a lung of patient 120.

Instrument 110 in the illustrated embodiment includes a drive mechanism 118, sometimes referred to herein as a backend mechanism 118, that converts electrical actuation signals from computer system 140 to kinematic responses in instrument 110 and/or that relays sensor signals from instrument 110 to computer system 140. Mechanism 118 may particularly include actuators and a mechanical interface for operation or actuation of mechanical systems such as joints in instrument 110. One implementation of mechanism 118 includes a transmission that converts rotations of actuator motors into movements or tensions in cables or tendons that extend from mechanism 118 to one or more joints that may be located along the length of instrument 110 or to a tool that may be located at distal tip 112. In an exemplary implementation where instrument 110 is a lung catheter, joints in a portion 114 of instrument 110 can be actuated, e.g., bent or flexed by drive mechanism 118, to control the position and orientation of distal tip 112 and the rigidity or stiffness of distal portion 114. U.S. Pat. App. Pub. No. 20110282491, dated Nov. 17, 2011, entitled "Drive Force Control in Medical Instrument Providing Position Measurements" and U.S. Pat. App. Pub. No. 2012/0123441, dated May 17, 2012, entitled "Tension Control in Actuation of Multi-Joint Medical Instruments," which are hereby incorporated by reference in their entirety, further describe some suitable computer assisted control systems and methods for controlling the tip orientation and stiffness of a flexible instrument such as a catheter.

Computer system 140 may execute a suitable program to generate the actuation signals based on sensor signals received from instrument 110, e.g., via a computer interface of mechanism 118, and based on control signals from one or more user interfaces or input devices. FIG. 1 shows an implementation including two input devices, a joy stick 142 and a foot pedal 144, which user 130 manipulates to provide control information to computer system 140. In particular, user 130 may manipulate joy stick 142 to cause computer system 140 and drive mechanism 118 to change the pitch and yaw angles of distal tip 112 and may manipulate foot pedal 144 to cause computer system 140 and drive mechanism 118 to change the stiffness of at least a portion 114 of instrument 110. In particular, foot pedal 144 may provide a proportional or an inverse proportional control signal to computer system 140, which adjusts the stiffness of the tip 114. For one case, as user 130 presses pedal 144 harder, tip 114 gets more compliant. When pedal 144 is fully depressed, tip 114 may turn to a completely floppy state, e.g., its most compliant state. For another case, tip 114 may get stiffer as user 130 further depresses pedal 144 and may be in its most compliant state when pedal 144 is not at all depressed. Stiffness can be controlled using other input devices. In particular, as described below, both steering and stiffness may be controlled through a single input device such as joystick 142, and foot pedal 144 may be omitted.

Mechanism 118 further includes an insertion drive system 150 that is operable to apply force along the length of instrument 110 for insertion or removal of instrument 110. Insertion drive system 150 may be operable in a computer assisted mode in which computer system 140 generates actuation signals that control actuated movement of insertion drive system 150 and a manual mode in which user 130 has direct contact with instrument 110 and manually controls movement of mechanism 118 along the insertion axis.

Insertion drive system 150 ideally provides mechanism 118 with low resistance and low inertia for movement in the insertion direction. In the illustrated implementation, insertion drive system 150 includes a track or ramp 152 and drive wheels 154 that engage track 152. Drive motors or other actuators (not shown) in mechanism 118 may rotate wheels 154 to move at least a portion of instrument 110 along track 152. Additionally or alternatively, track 152 may have an inclination angle that is adjustable to control gravitational forces on mechanism 118 and resulting insertion pressure. In particular, track 152 could be set at an inclination angle θ that is fixed to minimize resistance or overcome friction that resists movement of instrument tip 112 in the insertion direction. Alternatively, the inclination angle θ of track 152 can be dynamically adjusted to control the insertion force or according to the direction in which user 130 is manually guiding instrument 110. The inclination angle θ could thus be set before the procedure begins or adjusted, e.g., to minimize inertia or friction that resists insertion of instrument 110

In one implementation of a computer assisted mode, the actuator drive of insertion drive system 150 provides all of the insertion pressure. In one implementation of the manual mode, actuator drive in insertion drive system 150 is off of inactive. Manual insertion mode operation may, for example, be provided by turning off or inactivating drive motors in insertion drive system so that drive wheels 154 are freewheeling in manual insertion mode.

Figure 2:
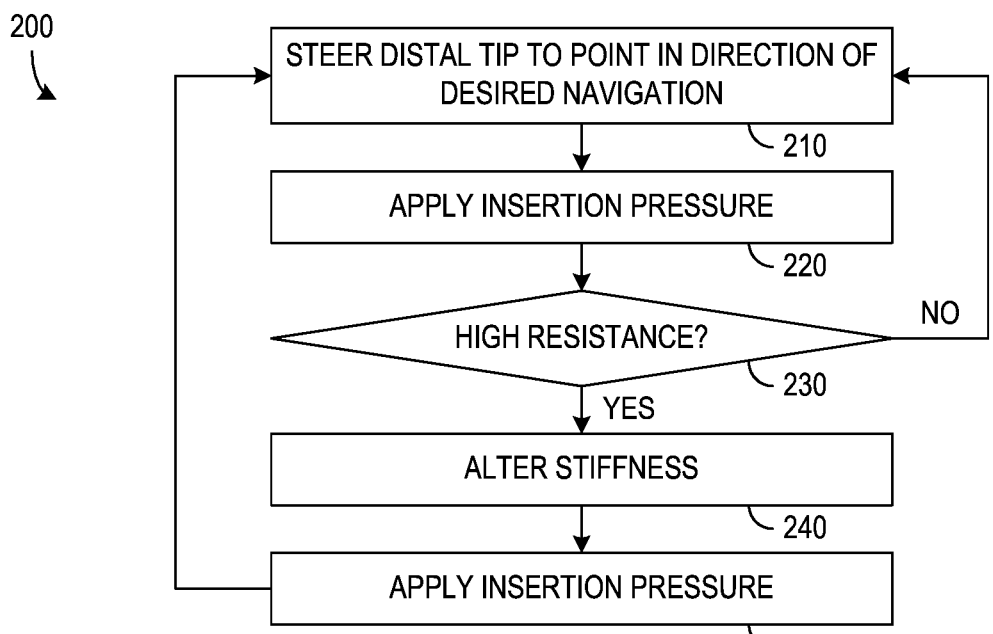
FIG. 2 is a flow diagram of a navigation process for a medical instrument.

One operating technique for system 100 includes controlling insertion of instrument 110 manually, while using computer assisted operation of instrument 110 to control the orientation of tip 112 and the stiffness of instrument 110. FIG. 2 is a flow diagram of one process 200 for operation of system 100 when instrument 110 is a lung catheter that needs to be navigated to a specific site in the airways of patient 120. During the airway navigation, user 130 steers catheter 110 by controlling the orientation of distal tip 112. For example, user 130 may employ a stereoscopic viewing system 145 that shows 3D images of the airways as captured by a vision system (not shown) at distal tip 112 or a display of sensor information indicating the position of distal tip 112, and based on such views or on position information, user 130 can steer distal tip 112 as represented in block 210 by manipulate joy stick 142 or other input device until distal tip 112 is oriented toward or along the airway that catheter 110 is to follow. User 130 can then manually apply insertion pressure as represented in block 220 by gripping a portion of instrument 110 and applying pressure to instrument 110 in the insertion direction. User 130 may, for example, continue to manually apply insertion pressure with one hand on instrument 110 while simultaneously using the other hand to operate joy stick 142 to steer distal tip 112.

During the insertion process, catheter-tissue interactions may occur and may prevent or resist the advancement of the catheter in an airway. While user 130 manually applies insertion pressure, user 130 can sense the amount of insertion pressure applied and the resistance and decide, as represented in block 230, whether resistance to insertion has increased, e.g., to a level that user 130 judges to be too high for the circumstances. If resistance is too high, for example, if the catheter gets stuck in the tissue, e.g., wedges in a tight lumen, user 130 can alter the stiffness of catheter 110 as represented in block 240. For example, user 130 can operate foot pedal 144 or another input device to reduce the level of rigidity or stiffness of at least distal portion 114 of instrument 110. In some medical systems, the stiffness of the catheter tip may be equivalent to a control parameter such as an applied control proportional gain parameter used in determining actuator response to user input. In other medical systems, instrument 110 may have joints that can be locked or loosened to change stiffness. Regardless of the specific mechanism for controlling stiffness, distal portion 114 may be made highly compliant during execution of block 240, which allows distal portion 114 to relax and conform to the shape of instrument 110 to the shape of the airway in which instrument 110 resides. When portion 114 relaxes, friction of instrument 110 against the walls of the airways may drop dramatically. Distal tip 112 of instrument 110 can then be inserted by manually applying pressure in block 250 before or after steering (block 210) is resumed. Relaxing the tip in block 240 will generally allow an instrument such as a catheter to move forward along the lumen direction when insertion pressure is applied. When steering resumes, the user can use (e.g., release) foot pedal 144 to increase the stiffness to permit steering or can keep moving the instrument forward in the low-stiffness state until the user needs to change the orientation of the tip, e.g., for airway navigation.

System 100 and process 200 can give user 130 haptic feedback while providing the precision advantage of robotically controlled instrument steering of the pitch-yaw orientation of distal tip 112. If instrument 110 gets stuck in a lumen such as an airway, user 130 may feel the resistance directly and immediately and react by adjusting the direction or orientation of tip 112 or by reducing the stiffness of tip 112 so that distal tip 112 can easily slide into a tight lumen without damaging or bumping on tissue.

System 100 of FIG. 1 and particularly insertion drive 150 may be operated in a fully robotically controlled mode when distal tip 112 nears a target site, e.g., a biopsy site for a biopsy needle. In particular, user 130 can switch system 100 to a computer assisted controlled mode in which both the insertion axis and the pitch-yaw can be controlled through joystick 142 or other input devices (not shown). The fully robotic controlled mode may particularly be desirable when a tool such as a biopsy needle is inserted through instrument 110 and user 130 desires that distal tip 112 be stable or precisely controlled.

Figure 3:
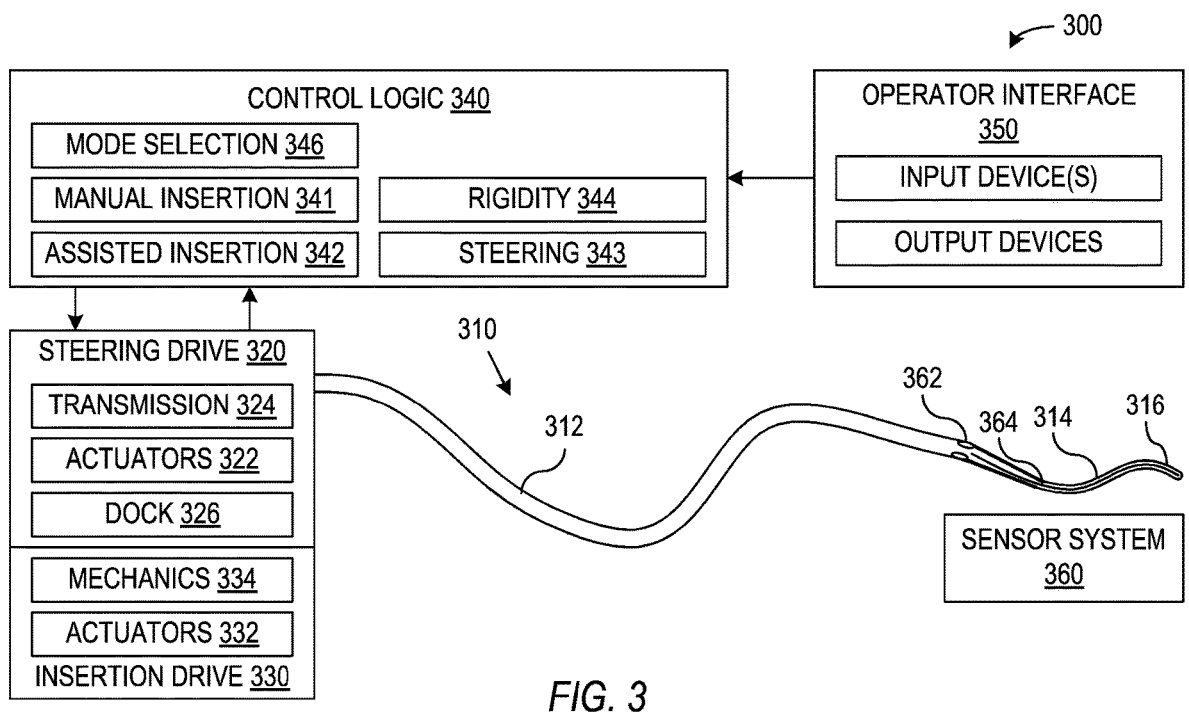
FIG. 3 is a block diagram of a medical system in accordance with another embodiment.

FIG. 3 schematically illustrates one specific implementation of a catheter system 300 that may operate as described above. In the illustrated implementation, catheter system 300 includes a lung catheter 310, a steering drive mechanism 320, an insertion drive mechanism 330, control logic 340, an operator interface 350, and a sensor system 360.

Figure 4:
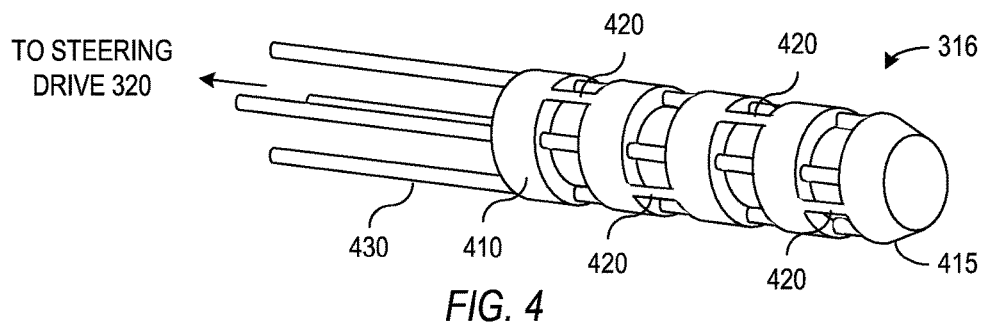
FIG. 4 shows one example of an implementation of a distal tip of a flexible instrument.

Catheter 310 is generally flexible and has one or more lumens including a main lumen that can accommodate interchangeable probes such as a biopsy needle or a vision system. Flexible catheters can be made using a braided structure such as a woven wire tube with inner or outer layers of a flexible or low friction material such as polytetrafluoroethylene (PTFE). In one embodiment, catheter 310 includes a bundle of lumens or tubes held together by a braided jacket and a reflowed (i.e., fused by melting) jacket of a material such as Polyether Block Amide (Pebax). An additional tip section 316 (e.g., a metal structure such as shown in FIG. 4 and described further below) can be attached as the distal end of catheter 310. In addition to the main lumen, catheter 310 may include smaller lumens for pull wires and sensor lines. In the illustrated embodiment, catheter 310 has a proximal section 312 attached to steering drive mechanism 320 and a distal section 314 that extends from proximal section 312. Proximal section 312 may include a gripping area that a user may grip in order to apply insertion pressure when system 300 operates in a manual insertion mode. Distal section 314 includes mechanical structure that may be actuated through pull wires that extend from steering drive mechanism 320 through proximal section 312 and distal section 314 and connect to steerable distal steerable segment 316.

The overall length of instrument 110 may be about 60 to 80 cm or longer with distal section 314 being about 15 cm long and steerable segment 316 being about 4 to 5 cm long. Distal section 314 may have a smaller diameter than does proximal section 312 to permit navigation of distal tip 316 into smaller natural lumens or passages. During a medical procedure, a portion of proximal section 312 and all of distal section 314 may be inserted along a natural lumen such as the throat and airway of a patient. The smaller diameter of distal section 314 permits use of distal section 314 in lumens that may be too small for proximal section 312, but the larger diameter of proximal section 312 may also facilitate manual manipulation.

Steerable segment 316 is remotely controllable and particularly has a pitch and a yaw that can be controlled using pull wires. Steerable segment 316 may include all or part of distal section 314 and may be simply implemented as a tube of flexible material such as Pebax. Ideally, steerable segment 316 is more flexible than the remainder of catheter 310 to assist in isolating actuation or bending to steerable segment 316 when steering drive mechanism 320 pulls on actuating tendons. Catheter 310 can also employ additional features or structures such as use of Bowden cables for actuating tendons to prevent actuation from bending proximal section 312 (or bending any portion of the section of 314 other than steerable segment 316) of instrument 110.

FIG. 4 shows one specific implementation of steerable segment 316. Steerable segment 316 in the implementation of FIG. 4 is made from a tube 410 that defines a main lumen for a probe system and defines smaller lumens, for example, for actuating tendons 430 and a shape sensor not shown in FIG. 4. In the illustrated embodiment, tendons 430 are placed 90° apart and surrounding lumen 312 to facilitate steering instrument 110 in pitch and yaw directions defined by the locations of tendons 430. A reflowed jacket, which is not shown in FIG. 4 to better illustrate the internal structure of steerable segment 316, may also cover tube 410. As shown in FIG. 4, tube 410 is cut or formed to include a series of flexures 420. Tendons 430 connect to a distal tip 415 of steerable segment 316 and extend back to steering drive mechanism 320. Tendons 430 can be wires, cables, Bowden cables, hypotubes, or any other structures that are able to transfer force from steering drive mechanism 320 to distal tip 415 and limit bending of proximal section 312 when steering drive mechanism 320 pulls on tendons 430. In operation, pulling harder on any one of tendons 430 tends to cause steerable segment 316 to bend in the direction of that tendon 430. To accommodate repeated bending, tube 410 may be made of a material such as Nitinol, which is a metal alloy that can be repeatedly bent with little or no damage.

Steering drive mechanism 320 of FIG. 3, which pulls on tendons 430 to actuate distal steerable segment 316, includes a mechanical system or transmission 324 that converts the movement of actuators 322, e.g., electric motors, into movements of (or tensions in) tendons 430 that run through catheter 310 and connect to distal steerable segment 316. (Push rods could conceivably be used in catheter 310 instead of pull wires but may not provide a desirable level of flexibility.) The movement and pose of distal steerable segment 316 can thus be controlled through computerized selection or generation of respective actuation signals for actuators 322 in steering drive mechanism 320. Control of the actuator force applied to tendons 430 can also control the effective stiffness or resistance to movement of steerable segment 316. In addition to actuation and stiffness control of steerable segment 316, steering drive mechanism 320 may be used to control other movement of catheter 310 such as rotation or roll of the proximal end of catheter 310, which may also be powered through actuators 322 and transmission 324. Backend mechanisms or transmissions that are known for flexible-shaft instruments could in general be used or modified for steering drive mechanism 320. For example, some known drive systems for flexible instruments are described in U.S. Pat. App. Pub. No. 2010/0331820, entitled "Compliant Surgical Device," which is hereby incorporated by reference in its entirety. Steering drive mechanism 320 in addition to actuating catheter 310 should allow removal and replacements of probes in the main lumen of catheter 310, so that the drive structure should be out of the way during such operations.

In the illustrated implementation of FIG. 3, steering drive mechanism 320 is mounted on insertion drive mechanism 330, which includes actuators 332 and a mechanical system 334 used to move steering drive mechanism 320 and catheter 310 along the insertion direction. Mechanical system 334 may be coupled to slide or carry steering drive mechanics 320 and may include track system with an adjustable incline such as described above. Actuators 332 may be drive motors that power movement of steering drive mechanics 320 and catheter 310 according to actuation signals selected by control logic 340.

Control logic 340 controls actuators 322 in steering drive mechanism 320 to selectively pull on the tendons as needed to actuate distal steerable segment 316 and control the orientation of the distal tip of catheter 310 and controls actuators 332 to control movement in the insertion direction of the distal tip of catheter 310. In general, control logic 340 operates in response to commands from a user, e.g., a surgeon, physician, or other medical personnel using operator interface 350, e.g., joy stick 142 and foot pedal 144, and in response to measurement signals from sensor system 360. However, in a manual insertion mode, control logic 340 may put actuators 332 of insertion drive system 330 in a free-wheeling state to allow the user to control insertion pressure. Control logic 340 may be implemented using a general purpose computer with suitable software, firmware, and/or device-specific interface hardware to interpret signals from operator interface 350 and sensor system 360 and to generate actuation signals for actuators 322 and 332.

In the illustrated embodiment, control logic 340 includes multiple modules 341, 342, 343, and 344 that implement different processes for different control modes or processes of catheter 310. As used herein, the term "module" refers to a combination of hardware (e.g., a processor such as an integrated circuit or other circuitry) and software (e.g., machine- or processor-executable instructions, commands, or code such as firmware, programming, or object code). A combination of hardware and software includes hardware only (i.e., a hardware element with no software elements), software hosted at hardware (e.g., software that is stored at a memory and executed or interpreted at a processor), or hardware and software hosted at hardware. Modules 341 and 342 respectively implement a manual insertion mode and a computer-assisted insertion mode. Module 343 may control steering with a stiffness level set by rigidity module 344. A module 346 selects which control processes will be used and may base the selection on factors such as user input, the type or status of the probe deployed in catheter 310, and the task being performed.

Operator interface 350 may include standard input/output hardware such as a vision system or display, a keyboard, a joystick, a foot pedal, a mouse, or other pointing device or similar I/O hardware that may be customized or optimized for a surgical environment. In general, operator interface 350 provides information to the user and receives instructions from the user. For example, operator interface 350 may indicate the status of system 300 and provide the user with data including images and measurements made by system 300. One type of instruction that the user may provide through operator interface 350, e.g., using a joystick or similar input device, indicates the desired movement, position, or orientation of distal steerable segment 316. The user may operate a foot pedal to indicate an amount or level of rigidity. Using such inputs, control logic 340 can generate actuation signals for actuators 322 in steering drive mechanism 320. Other instructions from the user can select an operating mode of control logic 340.

Figure 5:
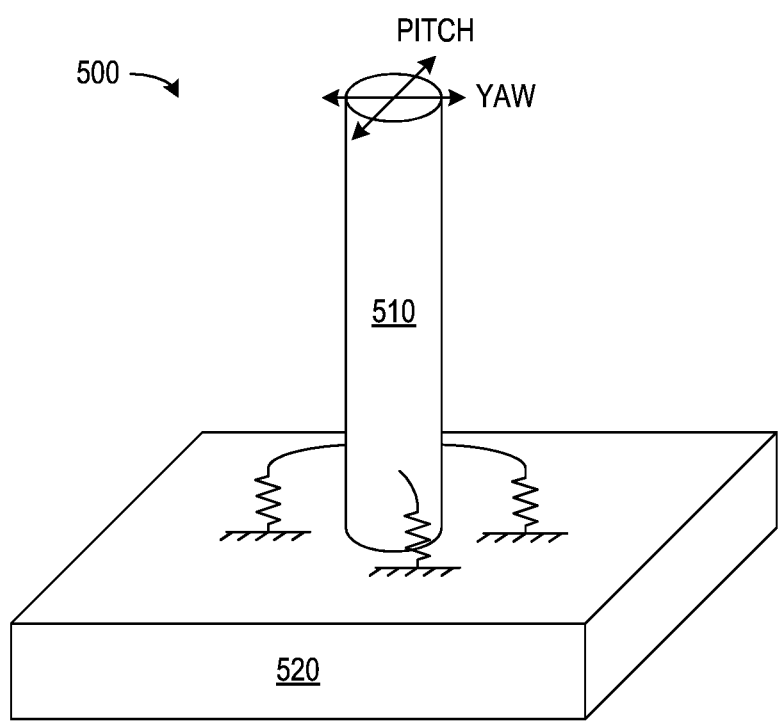
FIG. 5 shows a joystick suitable for controlling both steering and stiffness of a flexible instrument.

FIG. 5 shows a joy stick 500, which may be employed for steering of a flexible instrument as described above. In particular, a user may manipulate and tilt a stick portion 510 of joystick 500 in two dimensions relative to a base portion 520 of joystick 500 to indicate a pitch angle $\theta$ and a yaw angle $\psi$ or changes in pitch angle $\theta$ and a yaw angle $\psi$ desired for a distal tip of an instrument.

A medical system can also change the stiffness of a flexible instrument according to joystick input. In particular, stiffness can be a function of: displacement of stick 510 from a neutral position; pitch and yaw angles $\theta$ and $\psi$; or changes/velocity of pitch and yaw angles $\theta$ and $\psi$. In one particular implementation, a control system such as computer system 140 of FIG. 1 or control logic of 340 makes the stiffness of a flexible instrument its minimum value, e.g., by applying zero or minimum tension in drive tendons, when the joystick is in a neutral position and increases stiffness monotonically with increases in deflection of the joystick from the neutral position. The control system can select the neutral position of joystick 500 and can relax a flexible instrument into a low-stiffness or high-compliance state in which the flexible instrument conforms to its surrounding environment. When a user moves stick 510 away from the neutral position of joystick 500, the control system can increase the stiffness of the controlled instrument and change the orientation of the distal tip of the controlled instrument in a direct the user chose.

The neutral position of joystick 500 may be selected many ways. For example, the neutral position of joystick 500 may be: fixed, e.g., the position when no user force is applied to stick 510; set by the user, e.g., by the user pressing an input device such as a button or a foot pedal; or set by the control system based on analysis user movement of stick 510, e.g., set at a location at which the user has held stick 510 for a period of time.

The use of a joystick or similar input device to control both steering and stiffness may be employed with a flexible instrument and a medical system that may or may not provide a manual insertion mode. In particular, the ability to easily release the stiffness of a flexible instrument may be desirable even when the user is not manually inserting the instrument or when the user does not receive tactile sensation of the resistance of an instrument to being inserted.

Some implementations of medical instruments can provide the advantages of a fast navigation process for steering of the distal tip of an instrument to a biopsy site. Also, having a user receive direct haptic or tactile feedback may allow the user to accurately judge the amount of insertion pressure being applied and therefore minimize the chance of an automated system applying huge amount of force from the catheter to the tissue. The hands on feel of the insertion process may also give a user more confidence when navigating around airways.

Some embodiments of the above invention can be implemented in a computer-readable media, e.g., a non-transient media, such as an optical or magnetic disk, a memory card, or other solid state storage containing instructions that a computing device can execute to perform specific processes that are described herein. Such media may further be or be contained in a server or other device connected to a network such as the Internet that provides for the downloading of data and executable instructions.

Although particular implementations have been disclosed, these implementations are only examples and should not be taken as limitations. Various adaptations and combinations of features of the implementations disclosed are within the scope of the following claims.

What is claimed is:

1. A system comprising:
a flexible instrument;
control logic;
a first mechanism configured to control an orientation of a distal tip of the flexible instrument in response to a first signal from the control logic;
a second mechanism configured to move the flexible instrument along an insertion direction, wherein the control logic provides:
a first mode in which the second mechanism moves the flexible instrument along the insertion direction in response to a second signal from the control logic; and
a second mode in which the control logic allows manual control of movement of the flexible instrument along the insertion direction; and
a first input device operable by a user to generate the first signal, wherein the first input device has a neutral position, and wherein the control logic commands the flexible instrument to be in a low-stiffness state in response to the first input device being in the neutral position.

2. The system of claim 1, further comprising a second input device operable by a user to switch the system between the first mode and the second mode.

3. The system of claim 2, wherein the first input device comprises a joystick and the second input device comprises a pedal.

4. The system of claim 2, wherein the control logic uses user input provided through the second input device to control a stiffness of the flexible instrument.

5. The system of claim 1, wherein the first input device comprises a joystick.

6. The system of claim 5, wherein in response to user movement of the joystick away from the neutral position, the control logic commands stiffness of the flexible instrument to increase.

7. The system of claim 1, wherein in the second mode, the flexible instrument is commanded to have lower stiffness than when the system is in the first mode.

8. The system of claim 1, wherein the flexible instrument comprises an instrument selected from a group consisting of a lung catheter and a bronchoscope.

9. The system of claim 1, wherein the first input device enters the neutral position in response to a press of a button.

10. The system of claim 9, wherein the press of the button causes relaxation of the flexible instrument.

11. A navigation method comprising:
receiving a first input that defines a neutral position of an input device, the neutral position being adjustable;
receiving a second input from a user through the input device;
generating a signal based on the second input;
controlling, based on the signal, an orientation of a distal tip of a flexible instrument as the flexible instrument navigates a natural lumen;
controlling, based on the signal, a stiffness of the flexible instrument; and
decreasing the stiffness of the flexible instrument to a lowest stiffness in response to the input device being in the neutral position.

12. The method of claim 11, wherein controlling the orientation of the distal tip of the flexible instrument comprises:
commanding, according to the signal, an actuator that controls the orientation of the distal tip.

13. The method of claim 11, further comprising controlling, using computer assisted control, insertion of the flexible instrument through the natural lumen.

14. The method of claim 11, further comprising receiving a command to reduce the stiffness of the flexible instrument.

15. The method of claim 11, further comprising receiving a command to increase the stiffness of the flexible instrument.

16. The method of claim 11, wherein controlling the stiffness of the flexible instrument further comprises increasing the stiffness of the flexible instrument in response to the input device being moved away from the neutral position.

17. The method of claim 11, wherein receiving the first input that defines the neutral position includes:
receiving an indication that the input device has remained in a fixed position for a predetermined amount of time; and
defining the fixed position as the neutral position.

* * * * *

UNITED STATES PATENT AND TRADEMARK OFFICE
CERTIFICATE OF CORRECTION

PATENT NO. : 10,709,514 B2  
APPLICATION NO. : 15/509154  
DATED : July 14, 2020  
INVENTOR(S) : Au Page 1 of 1

It is certified that error appears in the above-identified patent and that said Letters Patent is hereby corrected as shown below:

On the Title Page

Item (57), should read as follows:
-- A system comprises a flexible instrument, control logic, and a first mechanism configured to control an orientation of a distal tip of the instrument in response to a first signal from the control logic. The system further comprises a second mechanism configured to move the instrument along an insertion direction. The control logic provides a first mode where the second mechanism moves the instrument along the insertion direction in response to a second signal from the control logic. The control logic further provides a second mode where the control logic allows manual control of movement of the instrument along the insertion direction. The system further comprises a first input device operable to generate the first signal. The first input device has a neutral position, and the control logic commands the instrument to be in a low-stiffness state in response to the first input device being in the neutral position. --

Signed and Sealed this  
Twenty-second Day of December, 2020

Andrei Iancu  
*Director of the United States Patent and Trademark Office*